United States Patent
Kalechofsky

(10) Patent No.: US 6,651,459 B2
(45) Date of Patent: Nov. 25, 2003

(54) HYPERPOLARIZATION OF A GAS

(75) Inventor: Neal Frederick Kalechofsky, Stow, MA (US)

(73) Assignee: Oxford Instruments Superconductivity Limited, Oxon (GB)

(*) Notice: Subject to any disclaimer, the term of this patent is extended or adjusted under 35 U.S.C. 154(b) by 0 days.

(21) Appl. No.: 10/182,189
(22) PCT Filed: Jan. 25, 2001
(86) PCT No.: PCT/GB01/00296
§ 371 (c)(1), (2), (4) Date: Nov. 25, 2002
(87) PCT Pub. No.: WO01/55656
PCT Pub. Date: Aug. 2, 2001

(65) Prior Publication Data
US 2003/0121279 A1 Jul. 3, 2003

(30) Foreign Application Priority Data
Jan. 25, 2000 (GB) ............................................. 0001727

(51) Int. Cl.$^7$ .................................................. F25J 1/00
(52) U.S. Cl. ...................................................... 62/601
(58) Field of Search ........................ 62/3.1, 55.5, 600, 62/601, 914

(56) References Cited

U.S. PATENT DOCUMENTS 5,617,860 A * 4/1997 Chupp et al. ............ 128/653.4
5,642,625 A * 7/1997 Cates, Jr. et al. ............ 62/55.5
5,809,801 A * 9/1998 Cates, Jr. et al. ............. 62/637

OTHER PUBLICATIONS

Frossati, "Polarization of $^3$He, D$_2$ (and possibly $^{129}$Xe) Using Cryogenic Techniques", Nuclear Instruments & Methods in Physics Research, Section—A: Accelerators, Spectrometers, Detectors and Associated Equipment, North–Holland Publishing Company, Amsterdam, NL, vol. 402, No. 2–3, Jan. 11, 1998, pp. 479–483.
G. Frossati, "Polarization of $^3$He, D$_2$, and (eventually) $^{129}$Xe Using Low Temperature and High Magnetic Fields", J. Low Temp. Phys., 1998, vol. III, No. 3–4, pp. 521–532.
Kauczor, et al., "MRI Using Hyperpolarized Noble Gases.", European Radiology, 1998, vol. 8, No. 5, pp. 820–827.
Kober, et al., "NMR Imaging of Thermally Polarized Helium–3 Gas", Journal of Magnetic Resonance, Jun. 1999, vol. 138, No. 2, pp. 308–312.
Chen et al., "Spatially Resolved Measurements of Hyperpolarized Gas Properties in the Lung in Vivo Part II: T*(2).", Magnetic Resonance in Medicine, Oct. 1999, vol. 42, No. 4, pp. 729–737.

* cited by examiner

Primary Examiner—Henry Bennett
Assistant Examiner—Malik N. Drake

(57) ABSTRACT

The present invention relates to a method of hyperpolarizing a gas sample. The method cryogenically forming a solidified gas structure from the sample gas, the solidified gas structure being surrounded by $^3$He. A magnetic field is then to the solidified gas structure and the $^3$He to thereby polarize the solidified gas structure, before the $^3$He is removed to thereby leave a solidified gas structure of hyperpolarized sample gas.

24 Claims, 1 Drawing Sheet

HYPERPOLARIZATION OF A GAS

Figure 1:
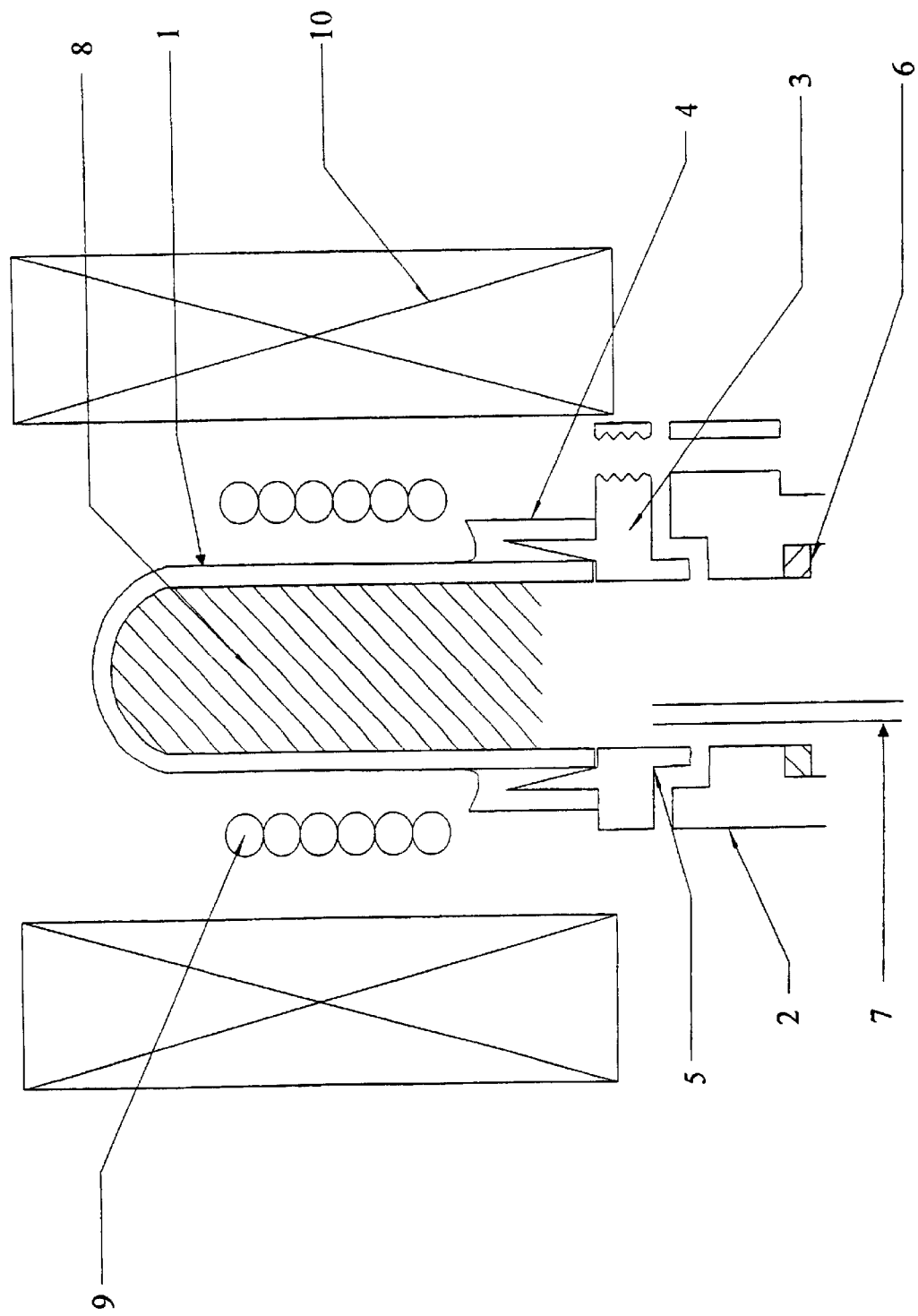

The present invention relates to a method and apparatus for hyperpolarizing a gas sample. In particular, the present invention relates to hyperpolarizing a noble gas for use in MRI and NMR experiments.

Conventional MRI techniques exploit the interaction of the intrinsic magnetic moment or spin of nuclei with an applied magnetic field. Nuclei whose spin is aligned with the applied magnetic field have a different energy state to nuclei whose spin is aligned opposed to the applied magnetic field. Accordingly, by applying a radio frequency radiation to the nuclei in a magnetic field, nuclei can be made to jump from a lower energy state to a higher energy state. The signals produced when the nuclei return to the lower energy state can then be measured, thereby providing information concerning the nature of the physical properties of the object being measured.

In most cases, MRI and NMR imaging is carried out using hydrogen nuclei which are present in water and fat. However, suitable nuclei are not always naturally present to enable measurements to be made. Thus, for example, in the lungs there are too few protons to generate a clear image. In addition to this microscopic air/tissue interfaces of the lung produce magnetic field variations that cause the already weak signal to decay even more rapidly. The problem is further exasperated by normal breathing and cardial motion.

A proposed solution to this is for the patient to inhale a mixture of a buffer gas, such as Nitrogen or Helium, and a strongly polarised sample gas, such as a noble gas. The hyperpolarized noble gas, as it is known, is a gas which includes an induced polarization, and hence an induced magnetic moment in the atomic nuclei. This allows MRI and NMR experiments to be performed in the normal way, even if the normally used hydrogen nuclei are not present.

Currently there are two main techniques for generating hyperpolarized gases. The first technique is described for example in U.S. Pat. No. 5,809,801, U.S. Pat. No. 5,617,860 and U.S. Pat. No. 5,642,625.

The technique described in these documents is the indirect hyperpolarization of Xenon or Helium3 ($^3$He). This is achieved by mixing the gas with a small amount of an alkaline-metal vapour, such as rubidium. A weak magnetic field is applied to the vapour mixture to cause splitting of the alkaline-metal electron energy levels.

The vapour mixture is then optically pumped using a laser to cause a build-up of electron polarization in the higher energy sub-level of the metal vapour. Nuclei of the noble gas atoms then become polarized by collisions with the alkaline-metal which causes transfer of angular momentum from the polarized alkali electrons to the nuclei spin of the noble gas.

An alternative method of hyperpolarizing $^3$He is achieved by direct optical pumping of a metastable state of the helium. In this method an electrical discharge and a low pressure cell are used to create atoms of $^3$He in a metastable state. These metastable atoms are then exposed to circularly polarized laser light, from a high powered LNA-laser, which causes the transfer of polarization from the electrons to the helium nuclei via coupling with the unpaired neutron.

Both of the above mentioned methods rely on optical pumping techniques and are therefore extremely inefficient.

Other methods have been considered which involve the use of solidified Xenon. However, the Xenon has a long spin-lattice relaxation time and therefore must be kept in a strong magnetic field, at a low temperature, for long periods of time to result in any useful level of polarization. This direct approach is therefore impractical.

In order to overcome this, the document "High Equilibrium Spin-Polarizations in Solid $^{129}$Xenon" by Honig et al, proposes mixing the Xenon with bulk amounts of oxygen to help improve the polarization. Meanwhile "The Brute Force $^{129}$Xe and D$_2$ Polarization at low temperature" by Usenko et al describes achieving polarization by inducing an electron current in the solidified Xenon. Again however, these techniques have proved to be extremely inefficient.

FROSSATI G: "Polarisation of He, D2 (and possibly Xe) using cryogenic techniques" NUCLEAR INSTRUMENTS & METHODS IN PHYSICS RESEARCH, SECTION—A: ACCELERATORS, SPECTROMETERS, DETECTORS AND ASSOCIATED EQUIPMENT, NORTH-HOLLAND PUBLISHING COMPANY AMSTERDAM, NL, vol. 402, no. 2–3, Jan. 11, 1998, pages 479–483 discloses a method of hyperpolarizing a gas sample, the method comprising the steps of cryogenically forming a solidified gas structure from the sample gas, the solidified gas structure being surrounded by 3He, applying a magnetic field to the solidified gas structure and the 3He to thereby polarize the solidified gas structure, and removing the 3He to thereby leave a solidified gas structure of hyperpolarized sample gas.

In accordance with a first aspect of the present invention, we provide a method of hyperpolarizing a gas sample, the method comprising the steps of:

a. cryogenically forming a solidified gas structure from the sample gas, the solidified gas structure being surrounded by $^3$He;

b. applying a magnetic field to the solidified gas structure and the $^3$He to thereby polarize the solidified gas structure; and c. removing the $^3$He to thereby leave a solidified gas structure of hyperpolarized sample gas, characterized in that step (c) comprises the steps of:
  i. increasing the temperature of the solidified gas structure;
  ii. introducing $^4$He into the region surrounding the solidified gas structure to thereby displace the $^3$He; and
  iii. pumping the $^3$He and the $^4$He away from the solidified gas structure.

In accordance with a second aspect of the present invention, we provide apparatus for hyperpolarizing a gas sample, the apparatus comprising:

a. cryogenic apparatus for forming a solidified gas structure from the sample gas, the solidified gas structure being surrounded by $^3$He;

b. magnetic field generating assembly for applying a magnetic field to the solidified gas structure and the $^3$He to thereby polarize the $^3$He and the solidified gas structure; and c. a removal system for removing the $^3$He to thereby leave a solidified gas structure of hyperpolarized noble gas, characterized in that the removal system is adapted to carry out the steps of:
  i. increasing the temperature of the solidified gas structure;
  ii. introducing $^4$He into the region surrounding the solidified gas structure to thereby displace the $^3$He; and
  iii. pumping the $^3$He and the $^4$He away from the solidified gas structure.

Accordingly, the present invention provides a method and an apparatus for producing a hyperpolarized sample gas. In this technique, a solidified gas structure is formed which is surrounded by $^3$He. A magnetic field is then applied to the gas structure and the $^3$He which causes polarization of the solidified gas structure. Under conditions of low temperature, solidified gases normally have an extremely low relaxation rate. However, in the present invention magnetic dipole—dipole coupling at the gas structure/$^3$He interface leads to an increase in the relaxation rate of the solidified gas, thereby increasing the rate at which the solidified gas is polarized. The $^3$He is then removed to leave behind a solidified gas structure of hyperpolarized noble gas. This can then be used in NMR and MRI experiments as required.

The step of cryogenically forming a solidified gas structure surrounded by $^3$He usually comprises the steps of forming a solidified gas structure and, introducing the $^3$He into the regions surrounding the solidified gas structure. Alternatively however the solidified gas structure is formed in an environment including $^3$He.

Typically the step of forming a solidified gas structure comprises the step of cooling a substrate within a chamber and, introducing the sample gas into the chamber thereby causing the sample gas to condense onto the substrate. However, alternatively the gas structure may be formed by introducing the sample gas into an environment including a substrate and then cooling the entire environment to cause the sample gas to condense onto the substrate.

Typically the introduction of the sample gas into the chamber is controlled such that the sample gas condenses to form a solidified gas layer on the substrate, the layer having a thickness of about 10 monolayers. This is particularly advantageous as the increased relaxation rate induced by the $^3$He is only effective for the uppermost layers of the solidified sample gas structure. Layers of the solidified gas further from the $^3$He will become polarized by spin diffusion effects which take time to propagate through the sample. For layers polarized by this technique, the effect of the $^3$He on the relaxation rate is reduced and it is therefore preferable to ensure that as much of the solidified gas structure as possible is in contact with the $^3$He to thereby ensure as high a relaxation rate as possible. However, thicker layers of noble gas may be used if the $^3$He is maintained in contact with the noble gas for longer periods of time.

It is preferable that the substrate is a porous medium so as to ensure the formation of a gas structure with a high surface area. Furthermore, it is preferable to ensure a low concentration of paramagnetic contaminants. Accordingly, the substrate is typically a fumed silica. However, any suitable substance having a high surface area could be used, such as activated carbon, exfoliated graphite, clays, porous glasses, zeolites, silica areogels, and silicas may also be used.

The solidified gas structure is preferably porous and has a large surface area. This ensures that as much of the noble gas as possible can be condensed and then polarized whilst interacting with the $^3$He thereby ensuring the polarization times are kept to a minimum. However, a reduced surface area could be used if other parameters such as the temperature of the substrate and the applied magnetic field are adjusted accordingly.

Typically the step of introducing the $^3$He into the region surrounding the solidified gas structure comprises precooling the solidified gas structure and, immersing the precooled solidified gas structure in liquid $^3$He. In this case, because the gas structure has a low heat capacity, it can be cooled to a temperature of below 4.2K and then immersed in the liquid $^3$He without causing an undue temperature rise in the $^3$He, which is itself typically cooled to a temperature of less than 100 mK and preferably to a temperature of 10 mK. This technique also ensures the entire surface of the solidified gas structure will be in contact with the $^3$He to ensure adequate bonding occurs. Furthermore, this allows the $^3$He to be maintained at a low temperature (below 100 mK) thereby overcoming the need to repeatedly cool the $^3$He.

However, the introduction of $^3$He into the area surrounding the gas structure may alternatively involve the steps of introducing the $^3$He into a chamber containing the solidified gas structure so as to fill the pores of the solidified gas structure and cooling the solidified gas structure to cause a $^3$He to solidify on the surface of the solidified gas structure. A further alternative is for the solidified gas structure may be precooled so that the $^3$He condenses and solidifies as soon as it has entered the chamber.

The method preferably further comprises cooling the solidified gas structure and the $^3$He to a temperature of less than 100 mK. In this case, the magnetic field applied to the solidified gas structure and the $^3$He has a strength of between 10 and 20T. However, alternative values of temperature and magnetic field can be used by adjusting other parameters to compensate for any reduction in the induced polarization. Thus for example, if a reduced magnetic field is used, the magnetic field could be applied for a longer periods of time. Ultimately however, the level of polarization will depend on the applied field and the inverse of temperature. It is therefore preferable to use as large a field as possible at a low temperature.

Typically the sample gas is a noble gas sample which comprises $^{129}$Xe. However, any suitable sample gas such as $^{131}$Xe, $^{83}$Kr $^{39}$Ar, $^{21}$Ne, $^{15}$N, $^2$D or the like, could be used. Accordingly, this does not represent an exhaustive list of the samples which can be polarised using the technique of the present invention.

Alternatively however, the sample gas could comprise $^3$He in which case, the $^3$He is preferably formed as a layer of solid on a substrate, with the solidified gas structure being surrounded by liquid $^3$He. This therefore allows hyperpolarized helium to be produced by the techniques of the present invention.

The method preferably further comprises the step of storing the hyperpolarized gas in the form of the solidified gas structure by maintaining the solidified gas structure in a magnetic field having a strength of between 50 mT and 1T at a temperature of below 10K. However, the gas may alternatively be vaporised and used immediately. The hyperpolarized gas can be obtained from the solidified gas structure by raising the temperature of the solidified gas structure to above 161K.

As previously described, the hyperpolarized gas is then suitable for use in NMR and MRI type analysis techniques. In the case of MRI, the hyperpolarized gas can be mixed with a buffer gas and then inhaled, allowing details of the lungs to be determined.

The cryogenic apparatus usually comprises a cell containing a porous substrate, the cell having an input for receiving the noble gas; a cooling system; and, a controller for controlling the cooling system, the controller being adapted to cause the cooling system to cool the cell thereby causing the noble gas to condense on the substrate so as to form a porous solidified gas structure.

Typically the removal system comprises a pump coupled to the cell, the controller operating to control the cooling system to raise the temperature of the cell so as to cause evaporation of the $^3$He, the pump being adapted to remove the $^3$He vapour from the cell. However, the controller could be adapted to raise the temperature of the cell to vaporise both the noble gas and the $^3$He. In this case, the apparatus would further comprise means for separating the resulting gas mixture.

Preferably the removal system further comprises a source of $^4$He, the source being coupled to the input to supply $^4$He into the cell, the $^4$He causing displacement of the $^3$He from the solidified gas structure. However, the removal of the $^3$He can be implemented without the addition of the $^4$He.

Typically the controller is also coupled to the magnetic field generating apparatus for controlling the magnetic field applied to the cell. This allows the applied field and the temperature of the solidified gas structure to be accurately controlled by a single element, thus ensuring that the solidified gas structure is subject to the ideal conditions for polarization.

The magnetic field generating apparatus will usually comprise at least one superconducting coil. However, several separate sets of coils may be used to ensure that fields of the desired strength and homogeneity can be generated for the entire solidified gas structure. As a result, the magnetic filed generating apparatus may also include permanent magnets.

An example of the present invention will now be described with reference to the accompanying drawing, which:

FIG. 1 is a schematic diagram of apparatus for generating a hyperpolarized noble gas in accordance with the present invention.

FIG. 1 shows a system suitable for generating a hyperpolarized gas in accordance with the present invention.

The system includes a cell 1 which is coupled to the cold end of a top loading refrigerator probe 2 via an attachment member 3. The entirety of the refrigerator probe system is not shown in the current drawing for clarity purposes although a pressed silver sinter seal 6 is shown which is used for coupling the probe 2 to the remainder of the refrigeration system.

The cell 1 is coupled to the attachment member 3 via a first seal 4 and the attachment member 3 is in turn coupled to the probe 2 via a second seal 5 which is typically formed from indium or the like.

The cell would typically include some pressed silver sinter to ensure good thermal contact with the probe 2.

Positioned at the open end of the cell 1 is a supply line 7 which is capable of supplying gases and liquids into the cell 1. A vacuum pump (not shown) is also provided for removing gases from inside the cell 1.

Finally, positioned around the cell 1 are a number of NMR coils 9 and a high-field magnetic generating assembly 10. These are controlled by separate driving circuits (not shown) as will be described in more detail below.

In this example, it will be noted that the cell 1 is a long thin cylinder. The use of a long thin cylinder is particularly advantageous as it will tend to minimise demagnetisation filled gradients which would arise if the cell included sharp corners, such as if it were rectangular in shape.

The cell typically has a volume in the region of 1 cm$^3$ although it will be appreciated that the apparatus can be scaled up to larger volume cells. With a cell of this size, in this example, the porous medium 8 is formed from approximately 0.1 gram of fumed silica which has an approximate surface area of 40 m$^2$.

The basic procedure for polarizing a noble gas, which in this example is $^{129}$Xe involves the following steps:

1. Coat the porous medium with $^{129}$Xe;
2. Coat the $^{129}$Xe with $^3$He;
3. Polarize the $^{129}$Xe;
4. Remove the $^3$He; and,
5. Store the hyperpolarized $^{129}$Xe.

Each of these procedures will now be explained in more detail below.

Coating the Porous Medium

Once the porous medium 8 is positioned in the cell 1, the cell 1 is pumped down to a vacuum using the vacuum pump and cooled. Once this has been completed, the $^{129}$Xe gas is introduced via the supply line 7.

As the $^{129}$Xe is introduced into the cell 1, the reduced temperature of the porous medium 8 causes the $^{129}$Xe to condense. This may be achieved under a variety of conditions.

A first example is to cool the cell 1 such that the porous medium 8 is held at a temperature of well below 100 Kelvin. The $^{129}$Xe gas is then admitted in a slow controlled manner so that $^{129}$Xe condenses directly onto the surface of the porous medium. At these temperatures the vapour pressure of the $^{129}$Xe is very small, and most atoms would remain where they first condense.

Another possible method is to hold the porous medium at a temperature between 100 Kelvin and the triple point 161 Kelvin as the $^{129}$Xe gas is admitted. At these temperatures the $^{129}$Xe condenses into a solid with an appreciable vapour pressure of up to 0.82 bar at the triple point. The presence of $^{129}$Xe vapour within the cell 1 allows for transport of $^{129}$Xe from one part of the porous medium to another, ideally ending up with a uniform film.

Thirdly, the porous medium may be maintained at a temperature above the triple point 161 Kelvin so that the $^{129}$Xe would initially condense into a liquid. This liquid would flow over the surface of the porous medium thereby ensuring even coating of the surface with $^{129}$Xe.

Alternatively, the $^{129}$Xe gas may be introduced into the cell 1 and then the cell 1 cooled to cause condensation of the $^{129}$Xe gas onto the surface of the porous medium.

Whichever conditions are used, the supply of the $^{129}$Xe is controlled so that the porous medium 8 is coated with a layer of approximately 10 monolayers thickness of $^{129}$Xe, i.e. approximately 40 Å thick.

Coating the $^{129}$Xe

Once the formation of the $^{129}$Xe coating has been achieved, the $^{129}$Xe coating must itself be coated with $^3$He. In this example, this is achieved by inserting $^3$He into the cell 1 through the supply line 7. This may be carried out under a variety of conditions.

Firstly, this can be performed at the temperature at which the $^{129}$Xe coating was condensed onto the porous medium, in which case the $^3$He is input as a gas. If this occurs, the cell 1 is then cooled to cause the $^3$He to liquify onto the $^{129}$Xe coating.

However, cooling the $^3$He to liquify it takes a long time and requires a large amount of energy. It is therefore preferable to introduce the $^3$He as a liquid. In order to achieve this the cell is pre-cooled to a temperature below 2.2K and preferably below 300 mK to ensure that the $^3$He remains in a liquid state. In this case, as the liquid $^3$He typically has a temperature of 10 mK, the introduction of the $^3$He advantageously causes further cooling of the cell 1, thereby ensuring the liquid $^3$He does not evaporate.

The liquid helium flows over the entire surface area of the $^{129}$Xe and binds to the $^{129}$Xe using the van der Waals interaction between the $^3$He and the solid molecules of $^{129}$Xe. This binding effectively pressurizes the first few layers of the $^3$He to above the solidification pressure which is 34 bar for $^3$He. This causes the formation of a solid layer of $^3$He on the surface of the $^{129}$Xe.

Due to the exceptionally small atomic polarizability of the $^3$He, the van der Waals forces are stronger between $^3$He and $^{129}$Xe atoms than between two $^3$He atoms. This not only makes the solidification of the $^3$He possible but also has consequences for eventual removal of the $^3$He, as will be explained in more detail below.

It will be realised that as an alternative, the $^{129}$Xe coating could be formed on the porous medium 8 which is then dipped into a "pool" of liquified $^3$He to ensure total coating of the $^{129}$Xe. In this case, the $^{129}$Xe would be precooled to a temperature of below 4K and the cell 1 could be removed from the probe 2. The cell can then be dipped in liquid $^3$He so as to coat the $^{129}$Xe before the cell 1 is replaced on the probe 2. In this case, with the liquid $^3$He being held at a temperature of below 300 mK, this would have the advantage that the $^{129}$Xe is further cooled by its immersion in the liquid $^3$He.

Polarization of the $^{129}$Xe

In most substances, the primary mechanism for nuclei magnetic relaxation is the modulation of the intermolecular dipole—dipole interaction by atomic or motion forces. Generally, this motion is nearly completely frozen out at dilution refrigerator temperatures leading to a very long relaxation time. However, in solid $^3$He, quantum tunnelling motion of the atoms at MHz frequencies leads to short relaxation times.

Accordingly, application of a magnetic field causes the relaxation of the $^3$He atoms in the solidified $^3$He layer, which in turn causes relaxation of the $^{129}$Xe atoms in the solidified $^{129}$Xe. However, due to the inverse cubed falloff of the dipole—dipole interaction with distance, it is only the surface layers of the solidified $^{129}$Xe which are effectively relaxed by the dipole—dipole interaction with the $^3$He atoms.

As will be appreciated by a person skilled in the art, the amount of relaxation in the $^{129}$Xe depends on the surface area of the $^{129}$Xe and the relative distance between the $^3$He and the $^{129}$Xe surface, as well as on the temperature, the applied magnetic field, and the duration for which the sample is held under the polarizing conditions.

Accordingly, providing the solidified $^{129}$Xe with a large surface area, and overlaying the $^3$He helps maximise the polarization.

Further improvement is also obtained by ensuring the cell 1 is cooled to about 10 mK. Once this has been completed, the $^3$He and the $^{129}$Xe exposed to a magnetic field having a strength in the region of 16T which is generated using the high strength magnet arrangement 10.

Under these conditions, suitable polarisation is achieved on a time scale of about 3000 s. However, it will be realised that these values can be varied significantly. For example, the longer the time used, the more the $^{129}$Xe becomes polarized. Thus, a reduced field could be used by maintaining the conditions for a longer period of time.

The level of polarisation of the sample is measured by the NMR coils 9, allowing the process to be stopped when the sample is sufficiently polarized.

Removal of the $^3$He

Once the $^{129}$Xe has been polarized using the above mentioned method, it is then necessary to remove the $^3$He. This is because, as the low temperature and high magnetic field conditions are removed, the $^3$He will rapidly relax and therefore lose polarization. This in turn would cause the polarization of the $^{129}$Xe to be reduced.

The most simple technique for removing the $^3$He is to heat the cell 1 to above 300 mK to cause the $^3$He to evaporate. This then allows the $^3$He to be removed from the cell 1 using the vacuum pump.

However, this technique suffers from the drawback that the solidified $^3$He layer that forms on the surface of the $^{129}$Xe will not evaporate at such low temperatures, due to the van der Waals interaction with the $^{129}$Xe atoms. Accordingly, to remove the solidified $^3$He it is necessary to further raise the temperature to about 4.2K to cause total evaporation of the $^3$He. By the time these temperatures have been attained and the $^3$He has evaporated, the $^{129}$Xe and $^3$He will have relaxed significantly, thereby causing a significant reduction in the polarization of the $^{129}$Xe.

As a result, it becomes necessary to store the resulting polarized $^{129}$Xe at temperatures of 4.2K under a magnetic field of 1T to ensure that the polarization remains for sufficiently long enough to allow the hyperpolarized $^{129}$Xe to be used.

However, this problem can be overcome by the introduction of $^4$He into the cell 1. This has two main effects.

Firstly, the $^4$He has no nuclei spin or dipole moment and therefore does not have relaxation enhancing properties of $^3$He.

Secondly, by virtue of its 33% great atomic mass and hence reduced quantum zero point motion, the $^4$He atoms will displace the $^3$He atoms from the solidified layer adjacent the $^{129}$Xe.

Accordingly, the addition of sufficient $^4$He causes displacement of the $^3$He such that $^4$He forms several monolayers on the surface of the polarized $^{129}$Xe. This is achieved by introducing the $^4$He at a temperature of below 2.2K and typically at about 300 mK so that the $^4$He forms a superfluid film that flows freely over the $^3$He. As more $^4$He is added, the $^4$He capillary condenses and covers the $^{129}$Xe so that the $^3$He is displaced.

The $^3$He can then be pumped out of the cell 1 using the vacuum pump. Due to the displacement of the solidified $^3$He, this allows the $^3$He to be removed by raising the temperature of the cell 1 to about 300 mK such that the liquid $^3$He evaporates, so that it can be pumped out.

Once this has been completed, the $^{129}$Xe can be separated from the $^4$He. This can be achieved in one of two ways.

Firstly, the cell 1 can be raised in temperature to above 2.2K so that the $^4$He evaporates and this in turn can be removed using the vacuum pump. This is possible because the $^4$He does not enhance the relaxation of the $^{129}$Xe and does not bind as strongly to the $^{129}$Xe as the $^3$He. Alternatively, the solid $^{129}$Xe can be removed from the cell 1 thereby leaving the liquid $^4$He in the cell.

Storing the Polarized $^{129}$Xe

Once the $^{129}$Xe has been separated from the $^3$He and/or the $^4$He the $^{129}$Xe can be stored. In order to prolong the presence of the polarization, it is necessary to store the $^{129}$Xe at low temperatures and in the presence of a magnetic field. The lower the temperatures and the higher the field then the longer the polarization can be maintained.

As mentioned above, if the $^3$He is removed by evaporation only, it is necessary to store the $^{129}$Xe at a temperature of 4.2K in a magnetic field of 1T.

However, if $^4$He has been used to displace the $^3$He then the $^{129}$Xe can be stored at a temperature of 4.2K in a magnetic field of approximately 100 mT in strength which can be generated by an additional coil arrangement (not shown) or by the high-field magnet arrangement 10.

In either case, this ensures that the $^{129}$Xe maintains a polarization sufficient for carrying out an MRI or NMR experiment for over 1 day.

It will be realised that the $^{129}$Xe can be stored in the cell 1, if the $^4$He has been removed. Alternatively, the $^{129}$Xe can be extracted from the cell 1, and transferred to an alternative storage facility.

When it is desired to use the $^{129}$Xe as a polarized gas in an MRI experiment, the solidified $^{129}$Xe can simply be heated in the presence of a magnetic field so that it evaporates into the vapour phase. When this occurs, although the relaxation time of the $^{129}$Xe will increase, the experiment can be arranged to use the $^{129}$Xe immediately so as to ensure that significant polarization remains.

Thus, for example, for MRI imaging of the lungs of a patient, the solidified $^{129}$Xe can be evaporated and warmed to room temperature. This can then be mixed with a suitable quantity of a buffer gas allowing the patient to breathe the mixture. MRI imaging can then be carried out by placing the patient in a magnetic field and performing the MRI procedure, in the normal way.

Additional Features Of The Invention

The above example was described with respect to the use of $^{129}$Xe as the sample gas being polarized. However, the present invention can be applied to any noble gas and to other gas samples such as $^2$D or the like.

The present invention can also be utilized to obtain polarized $^3$He in two main ways.

Firstly, if $^4$He is used as a relaxation switch to remove the $^3$He from the $^{129}$Xe surface in the above described example, then the removed $^3$He will typically have a level of polarization higher than that of the $^{129}$Xe. The $^4$He and $^3$He can therefore be removed from the cell 1 to provide a gas mixture comprising hyperpolarized $^3$He, together with $^4$He. In this circumstance, the $^4$He acts as a buffer to help prevent depolarization of the $^3$He. Accordingly, the $^3$He and $^4$He can be removed from the cell 1 and subsequently separated to provide pure hyperpolarized $^3$He.

Secondly, it is possible to hyperpolarize $^3$He using the techniques outlined in the examples above by replacing the $^{129}$Xe coated with $^3$He, with a layer of solidified $^3$He which has been formed on a cold surface, such as the porous medium 8.

As in the example described above with respect to $^{129}$He, the layer of solid $^3$He is formed by coating the cooled porous medium 8. When the solid $^3$He layer is formed, additional liquid $^3$He is usually present in the surrounding region, as not all the $^3$He will be close enough to form strong Van der Waals bonds with the porous medium.

Once the solidified $^3$He layer has formed, because the solid $^3$He has a favourable relaxation rate, the solidified $^3$He can be polarized by applying a magnetic field to the sample under suitable temperature conditions (typically less than 2.2K).

Once the solidified $^3$He layer has been polarized, it is then necessary to remove the surrounding liquid $^3$He which will not have polarized so easily. It should be noted that the solid $^3$He follows a Curie law for magnetization whereas the liquid $^3$He follows a Pauli law and accordingly, for a given field over temperature ratio, the solid $^3$He polarises far easier.

In order to remove the liquid $^3$He, liquid $^4$He is introduced in to the cell 1. The liquid $^4$He displaces the liquid $^3$He from the solid $^3$He and the resultant $^3$He and $^4$He mixture can then be heated and removed, in the manners described above with respect to the $^{129}$Xe example.

The polarized solidified $^3$He can then be removed from the cell, by heating the cell to allow the $^3$He to liquify or evaporate, in an applied magnetic field, as was described above with respect to the $^{129}$Xe.

Accordingly, it will be appreciated by a person skilled in the art that the technique used to polarize the $^{129}$Xe can also be used to polarize the $^3$He.

What is claimed is:

1. A method of hyperpolarizing a gas sample, the method comprising the steps of:
   a. cryogenically forming a solidified gas structure from the sample gas, the solidified gas structure being surrounded by $^3$He;
   b. applying a magnetic field to the solidified gas structure and the $^3$He to thereby polarize the solidified gas structure; and
   c. removing the $^3$He to thereby leave a solidified gas structure of hyperpolarized sample gas, characterized in that step (c) comprises the steps of:
      i. increasing the temperature of the solidified gas structure;
      ii. introducing $^4$He into the region surrounding the solidified gas structure to thereby displace the $^3$He; and
      iii. pumping the $^3$He and the $^4$He away from the solidified gas structure.

2. A method according to claim 1, wherein step (a) comprises the stepsof:
   i. forming a solidified gas structure; and
   ii. introducing the $^3$He into the region surrounding the solidified gas structure.

3. A method according to claim 2, wherein step (ai) comprises the steps of:
   (1) cooling a substrate within a chamber; and,
   (2) introducing the sample gas into the chamber thereby causing the sample gas to condense onto the substrate.

4. A method according to claim 3, wherein the introduction of the sample gas into the chamber is controlled such that the sample gas condenses to form a solidified gas layer on the substrate, the layer having a thickness of about 10 monolayers.

5. A method according to claim 3, wherein the substrate is a fumed silica.

6. A method according to claim 2, the solidified gas structure being porous and having a large surface area.

7. A method according to claim 6, wherein step (aii) comprises the steps of:
   (1) precooling the solidified gas structure; and,
   (2) immersing the precooled solidified gas structure in liquid $^3$He.

8. A method according to claim 7, wherein solidified gas structure is precooled to a temperature of below 4.2K.

9. A method according to claim 7, wherein the liquid $^3$He is precooled to a temperature of below 100mK.

10. A method according to claim 1, wherein step (a) comprises forming a solid layer of $^3$He on the solidified gas structure.

11. A method according to claim 1, wherein step (a) further comprises cooling the solidified gas structure and the $^3$He to a temperature of less than 100 mK.

12. A method according to claim 1, wherein the magnetic field applied during step (b) has a strength of between 10T and 20T.

13. A method according to claim 1, wherein the gas sample is a noble gas.

14. A method according to claim 13, wherein the gas sample comprises $^{129}$Xe.

15. A method according to claim 13, the method further comprising heating the solidified gas structure to a temperature greater than 161K to obtain a hyperpolarized noble gas.

16. A method according to claim 1, the method further comprising the step of storing the hyperpolarized gas in the form of the solidified gas structure by maintaining the solidified gas structure in a magnetic field having a strength of between 50 mT and 1T at a temperature of below 10K.

17. A method of performing an NMR experiment, the method comprising supplying a hyperpolarized gas generated according to claim 1 to a cavity to be analysed and performing an NMR experiment.

18. Apparatus for hyperpolarizing a gas sample, the apparatus comprising:
   a. cryogenic apparatus for forming a solidified gas structure from the sample gas, the solidified gas structure being surrounded by $^3$He;
   b. magnetic field generating assembly for applying a magnetic field to the solidified gas structure and the $^3$He to thereby polarize the $^3$He and the solidified gas structure; and
   c. a removal system for removing the $^3$He to thereby leave a solidified gas structure of hyperpolarized noble gas, characterized in that the removal system is adapted to carry out the steps of:
      i. increasing the temperature of the solidified gas structure;
      ii. introducing $^4$He into the region surrounding the solidified gas structure to thereby displace the $^3$He; and
      iii. pumping the $^3$He and the $^4$He away from the solidified gas structure.

19. Apparatus according to claim 18, wherein the cryogenic apparatus comprises:
   a cell containing a porous substrate, the cell having an input for receiving the sample gas;
   a cooling system; and,
   a controller for controlling the cooling system, the controller being adapted to cause the cooling system to cool the cell thereby causing the sample gas to condense on the substrate so as to form a porous solidified gas structure.

20. Apparatus according to claim 19, wherein the substrate is formed from a fumed silica.

21. Apparatus according to claim 19, the removal system comprising a pump coupled to the cell, the controller operating to control the cooling system to raise the temperature of the cell so as to cause evaporation of the $^3$He, the pump being adapted to removed the $^3$He vapour from the cell.

22. Apparatus according to claim 21, wherein the removal system further comprises a source of $^4$He, the source being coupled to the input to supply $^4$He into the cell, the $^4$He causing displacement of the $^3$He from the solidified gas structure.

23. Apparatus according to claim 19, wherein the controller is coupled to the magnetic field generating apparatus for controlling the magnetic field applied to the cell.

24. Apparatus according to claim 18, wherein the magnetic field generating apparatus comprises at least one superconducting coil.

* * * * *